United States Patent [19]
Fomenkov et al.

[11] Patent Number: 5,498,535
[45] Date of Patent: Mar. 12, 1996

[54] **METHOD FOR DIRECT CLONING OF NUCLEASE GENES IN *E. COLI***

[75] Inventors: Aleksei Fomenkov, Beverly; Deborah K. Dila, Boston; Elisabeth A. Raleigh, Somerville; Shuang-Yong Xu, Lexington, all of Mass.

[73] Assignee: New England Biolabs, Inc., Beverly, Mass.

[21] Appl. No.: 247,990

[22] Filed: May 24, 1994

[51] Int. Cl.$^6$ .......................... C12N 15/55; C12N 15/70; C12N 9/22
[52] U.S. Cl. .................. 435/172.3; 435/252.33; 435/199
[58] Field of Search .................... 435/199, 193, 435/172.3, 19, 34, 252.33; 935/82, 84

[56] References Cited

U.S. PATENT DOCUMENTS 5,200,333  4/1993  Wilson ................. 435/172.3

OTHER PUBLICATIONS

Fomenkov, A, et al. (1994) Nucl. Acids Res 22(12) 2399–2403.
Kosykh, et al., Molec. Gene. Genet. 178:717–718 (1980).
Mann, et al., Gene, 3:97–112 (1978).
Walder, et al., Proc. Natl. Acad. Sci. USA, 78:1503–1507 (1981).
Bougueleret, et al., Nucl. Acid. Res., 12:3659–3676 (1984).
Gingeras and Brooks, Proc. Natl. Acad. Sci. USA, 80:402–406 (1983).
Theriault and Roy, Gene, 19:355–359 (1982).
Blumenthal, et al., J. Bacteriol., 164:501–509 (1985).
Kiss, et al., Nucl. Acid. Res., 13:6403–6421 (1985).
Szomolanyi, et al., Gene, 10:219–225 (1980).
Janulaitis, et al., Gene, 20:197–204 (1982).
Kiss and Baldauf, Gene, 21:111–119 (1983).
Walder, et al., J. Biol. Chem., 258:1235–1241 (1983).
Raleigh and Wilson, Proc. Natl. Acad. Sci. USA, 83:9070–9074 (1986).
Heitman and Model, Gene, 103:1–9 (1991).
Kelleher and Raleigh, J. Bacteriol. 173:5220–5223 (1991).
Kenyon and Walker, Proc. Natl. Acad. Sci. USA, 77:2819–2823 (1980).
Heitman and Model, J. Bacteriol., 169:3243–3250 (1989).
Pierkarowicz, et al., J. Bacteriol. 173:150–155 (1991).
Pierkarowicz, et al., Nucl. Acids Res., 19:1831–1835 (1991).
Panayotatos and Fontaine, J. Biol. Chem., 260:3173–3177 (1985).
Xu and Schildkraut, J. Biol. Chem., 266:4425–4429 (1991).
Heitman, et al., Proc. Natl. Acad. Sci. USA, 86:2281–2285 (1989).

*Primary Examiner*—Charles L. Patterson, Jr.
*Attorney, Agent, or Firm*—Gregory D. Williams

[57] ABSTRACT

The present invention discloses a novel method for the direct cloning of nuclease genes such as restriction endonuclease genes in *E. coli*. In addition, there is provided a novel strain which facilitates application of the method. This method has been successfully employed to clone a number of genes coding for endonuclease including restriction endonuclease genes.

12 Claims, 2 Drawing Sheets

METHOD FOR DIRECT CLONING OF NUCLEASE GENES IN E. COLI

BACKGROUND OF THE INVENTION

Nucleases are a class of enzymes which degrade or cut single- or double-stranded DNA. Restriction endonucleases are an important class of nucleases which recognize and bind to particular sequences of nucleotides (the 'recognition sequence') along the DNA molecule. Once bound, they cleave both strands of the molecule within, or to one side of, the recognition sequence. Different restriction endonucleases recognize different recognition sequences. Over one hundred and eighty restriction endonucleases with unique specificities have been identified among the many hundreds of bacterial species that have been examined to date.

It is thought that in nature, restriction endonucleases play a protective role in the welfare of the bacterial cell. They enable bacteria to resist infection by foreign DNA molecules like viruses and plasmids that would otherwise destroy or parasitize them. They impart resistance by cleaving invading foreign DNA molecules when the appropriate recognition sequence is present. The cleavage that takes place disables many of the infecting genes and renders the DNA susceptible to further degradation by non-specific endonucleases.

A second component of these bacterial protective systems are the modification methylases. These enzymes are complementary to the restriction endonucleases and they provide the means by which bacteria are able to protect their own DNA from cleavage and distinguish it from foreign, infecting DNA. Modification methylases recognize and bind to the same nucleotide recognition sequence as the corresponding restriction endonuclease, but instead of cleaving the DNA, they chemically modify one or other of the nucleotides within the sequence by the addition of a methyl group. Following methylation, the recognition sequence is no longer bound or cleaved by the restriction endonuclease. The DNA of a bacterial cell is always fully modified by virtue of the activity of the modification methylase. It is therefore completely insensitive to the presence of the endogenous restriction endonuclease. It is only unmodified, and therefore identifiably foreign DNA, that is sensitive to restriction endonuclease recognition and cleavage.

With the advent of genetic engineering technology, it is now possible to clone genes and to produce the proteins and enzymes that they encode in greater quantities than are obtainable by conventional purification techniques. The key to isolating clones of restriction endonuclease genes is to develop a simple and reliable method to identify such clones within complex 'libraries', i.e. populations of clones derived by 'shotgun' procedures, when they occur at frequencies as low as $10^{-3}$ to $10^{-4}$.

Type II restriction-modification systems are being cloned with increasing frequency. The first cloned systems used bacteriophage infection as a means of identifying or selecting restriction endonuclease clones (Eco RII: Kosykh et al., *Molec. Gen. Genet.* 178:717–719, (1980); Hha II: Mann et al., *Gene* 3:97–112, (1978); Pst I Walder et al., *Proc. Nat. Acad. Sci.* 78:1503–1507, (1981)). Since the presence of restriction-modification systems in bacteria enables them to resist infection by bacteriophages, cells that carry cloned restriction-modification genes can, in principle, be selectively isolated as survivors from libraries that have been exposed to phage. This method has been found, however, to have only limited value. Specifically, it has been found that cloned restriction-modification genes do not always manifest sufficient phage resistance to confer selective survival.

Another cloning approach involves transferring systems initially characterized as plasmid-borne into E. coli cloning plasmids (Eco RV: Bougueleret et al., *Nucl. Acid. Res.* 12: 3659–3676, (1984); Pae R7: Gingeras and Brooks, *Proc. Natl. Acad. Sci. USA* 80:402–406, (1983); Theriault and Roy, *Gene* 19:355–359 (1982); Pvu II: Blumenthal et al., *J. Bacteriol.* 164:501–509, (1985)).

A third approach, and one that is being used to clone a growing number of systems are now being cloned by selection for an active methylase gene. See, e.g., U.S. Pat. No. 5,200,333, and Bsu RI: Kiss et al., *Nucl. Acid. Res.* 13:6403–6421, (1985)). Since restriction and modification genes are often closely linked, both genes can often be cloned simultaneously. This selection does not always yield a complete restriction system however, but instead yields only the methylase gene (Bsp RI: Szomolanyi et al., *Gene* 10: 219–225, (1980); Bcn I: Janulaitis et al, *Gene* 20: 197–204 (1982); Bsu RI: Kiss and Baldauf, *Gene* 21: 111–119, (1983); and Msp I: Walder et al., *J. Biol. Chem.* 258: 1235–1241, (1983)).

A fourth cloning method (the "methylase indicator" method) relies on methylation-dependent restriction systems McrA, McrBC, and Mrr (Raleigh and Wilson, *Proc. Natl. Acad. Sci., USA* 83: 9070–9074, (1986), Heitman and Model, *Gene.* 103:1–9; Kelleher and Raleigh, *J. Bacteriol.* 173:5220–5223, (1991)) and the dinD1::lacZ operon fusion to screen for clones that contain methylase genes. The dinD1 locus is a DNA damage inducible gene that is expressed in E. coli when the "SOS response" is triggered, as by UV treatment, mitomycin treatment, or the action of McrA, McrBC, or Mrr restriction endonucleases on methylated DNA (Kenyon and Walker, *Proc. Natl. Acad. Sci. USA,* 77:2819–2823, (1980), Heitman and Model, *Gene,* 103:1–9, (1991); Heitman and Model, *J. Bacteriol.* 169:3234–3250, (1989); and Piekarowicz et al. *J. Bacteriol.* 173:150–155, (1991), the disclosures of which are incorporated herein by reference). Strains with temperature sensitive mutations in mcrA, mcrBC, mrr and carrying the dinD1::lacZ fusion were constructed and used for the direct cloning of methylase genes into E. coli from other bacterial sources (Piekarowicz et al., *Nucleic Acids Res.* 19:1831–1835, (1991), the disclosure of which is incorporated herein by reference). Upon transformation of ligated genomic/vector DNA into such strain, transformants containing a gene expressing a methylase that confers sensitivity to one of the methylation-dependent restriction systems form white colonies at 42° C. and blue colonies at 30° C. on X-gal indicator plates as a result of methylation-dependent restriction that results in SOS DNA repair induction and β-galactosidase expression. Because of close linkage between most restriction enzyme genes and the cognate methylase genes, cloning of a methylase gene in a DNA fragment of reasonable size may lead to concomitant cloning of the cognate endonuclease gene.

It would be desirable to design a method for the direct cloning of nucleases, such as restriction endonucleases, as an alternative method when standard approaches are either impractical or fail to yield positive results.

SUMMARY OF THE INVENTION

In accordance with the present invention, there is provided a novel method for the direct cloning of nuclease genes such as restriction endonuclease genes in E. coli. In addition, there is provided a novel strain which facilitates application of the above method. This method has been successfully employed to clone a number of genes coding for nucleases including restriction endonuclease genes.

More specifically, the present invention relates to (i) a new E. coli strain containing the dinD1::lacZ fusion, which strain is deficient in all restriction systems, (EcoKR−, McrA−, McrBC−, Mrr−), (ii) a method for direct cloning of nuclease genes in E. coli using a strain which contains a fusion of a DNA damage-inducing promoter and an indicator/reporter gene such as the dinD1::lacZ fusion, and (iii) isolated DNA coding for certain nucleases cloned by this method. As it has been shown that DNA breaks or nicks introduced by the T7.3 endonuclease, Eco RI, or Bam HI restriction enzymes induce the SOS response in E. coli. (Panayotatos and Fontaine, J. Biol. Chem. 260:3173–3177, (1985), Heitman and Model, Gene, 103:1–9, (1991), Xu and Schildkraut, J. Biol. Chem. 266:4425–4429, (1991)), the present inventors reasoned that when ligated genomic DNA fragments and vector are introduced into an indicator strain such as dinD1::lacZ deficient in all restriction systems so far described and transformants plated on X-gal plates, one might find the nucleases-containing clone directly by picking blue colonies. When used to clone genes coding for a restriction endonuclease, unlike the methylase selection approach, it is not necessary that the methylase gene fully protect the host chromosome. In fact, the methylase gene may be absent altogether. This is particularly true for thermostable enzymes where, in accordance with the present invention, the transformants are grown at lower temperatures, i.e., between about 30°–37° C. At this lower temperature, thermostable restriction endonucleases are less active, and transformed host cells may survive with partial or even without protective methylation.

In other words, in accordance with the method of the present invention, when host cells such as the preferred E. coli cells (dinD1::lacZ, EcoKR−, McrA−, McrBC−, Mrr−) are transformed with ligated genomic/vector DNA and transformants are plated on X-gal plates, cells carrying the restriction endonuclease gene form blue colonies because the restriction enzyme damages DNA in vivo and induces the SOS DNA repair response. This method (the "endonuclease indicator method") differs from the "methylase indicator method", Piekarowicz et al., supra, in that the earlier method detected expression of the methylase, not the endonuclease. That method relied on the DNA-damaging action of endogenous restriction enzymes (McrA, McrBC or Mrr) that act on specific methylated sequences. Expression of an appropriate foreign methylase can create a sequence susceptible to one or more of these methylation-specific endonucleases, leading to SOS-induction and blue color. The gene for the cognate endonuclease might or might not accompany the methylase gene. The endonuclease indicator method of the present invention detects the endonuclease only and not the methylase, because the relevant methylation-dependent restriction systems are absent from the host. The genes coding for the thermostable restriction enzymes Taq I (5'TCGA3') and Tth 111I (5'GACNNNGTC3') have been successfully cloned in E. coli by this method. The methylase selection method (Szomolanyi et al. Gene 10: 219–225, (1980) and the "endonuclease indicator method" can also be combined to clone restriction endonuclease genes. The gene coding for the restriction endonuclease ecoO109IR has been cloned by combining these two methods.

DETAILED DESCRIPTION OF THE INVENTION

Figure 1:
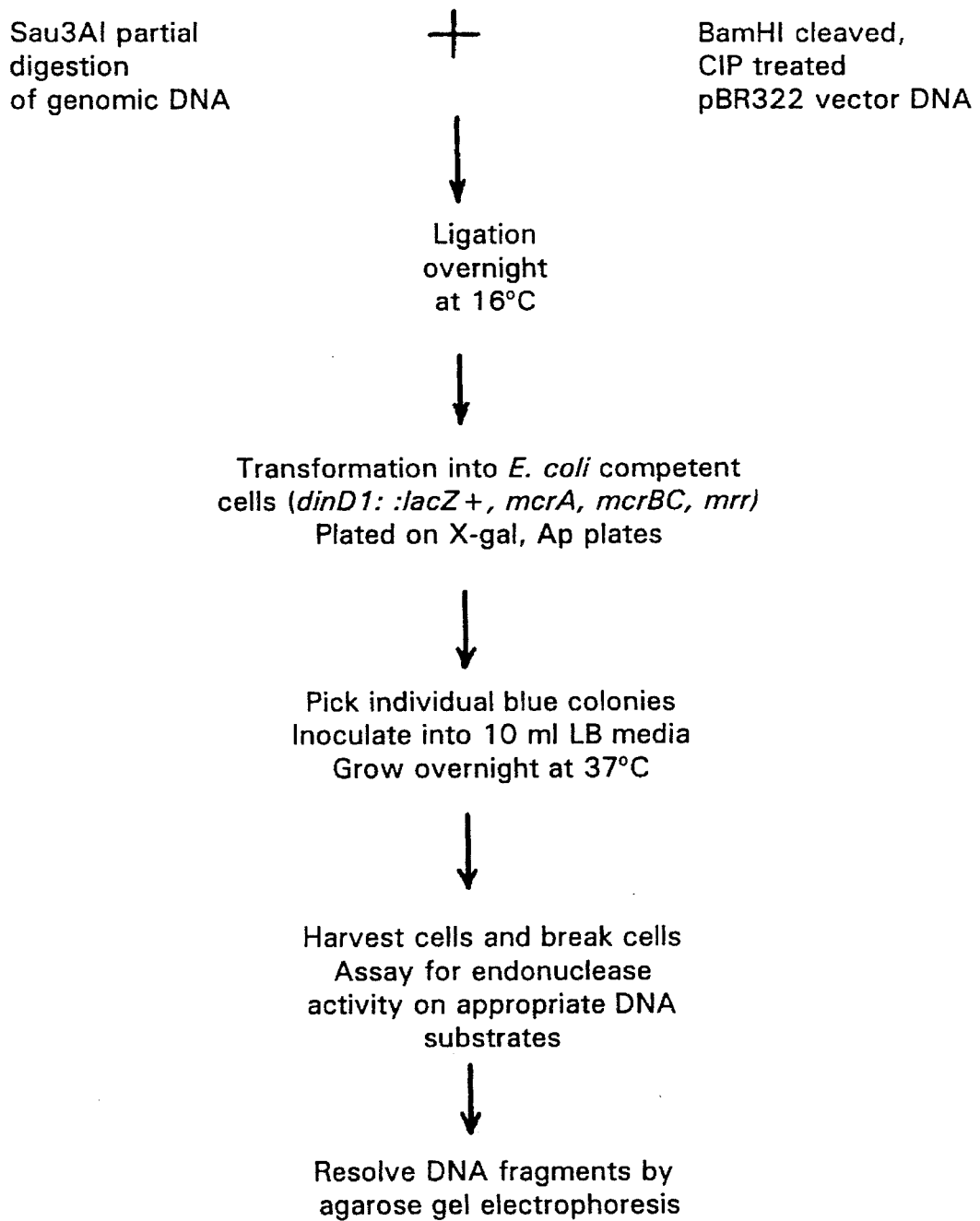
FIG. 1 is a scheme for the cloning of tth111IR gene, the gene coding for Tth111I, in E. coli.

In accordance with one embodiment of the invention, there is provided a novel method for the direct cloning of nuclease genes. In general, the method comprises the following steps, although as the skilled artisan will appreciate, modifications to these steps may be made without adversely affecting the outcome:

1) Genomic DNA is prepared from the nuclease producing strain and cleaved completely or partially to generate about 500 bp–20,000 bp clonable DNA fragments. These fragments may be obtained, for example, with restriction enzymes or sheared by sonication. The fragments so obtained are thereafter ligated to cloning vectors with compatible cohesive ends or blunt ends in pBR322, pUC19, pACYC187, pSC101, or their derivatives.

2) The ligated DNA mixture is transferred into a bacterial strain which contains a DNA damage-producing promoter fused to an indicator/reporter such as the preferred dinD::lacZ fusion and which is deficient in methylation-dependent restriction systems (dinD::lacZ, hsdR, mcrA, mcrBC, mrr). One preferred strain is E. coli ER1992 (NEB #907), a sample of which has been deposited at the American Type Culture Collection under the terms of the Budapest Treaty on May 24, 1994, ATCC Accession No. 55582. Other DNA damage-inducing promoters which can be used include dinA (Iwasaki, M., et al., J. Bacteriol., 172:6268–6273 (1990) and dinG (Lewis, L. K., J. Bacteriol. 174:5110–5116 (1992), the disclosures of which are incorporated herein by reference. Other indicator/reporter genes which can be fused to any of the above promoters include alkaline phosphatase (phoA) (Proc. Natl. Acad. Sci. USA, 82:5107–5111 (1985), luciferase (lux) (Engelrecht, J., Science, 227:1345–1347 (1985), β-glucuronidase (Metcalfe, W. W., Gene, 129:17–25 (1993), aminoglycoside phosphotransferase (Ward, J. M., et al., Mol. Gen. Genet., 203:468–478 (1986), and endoglucanase (Bingle, W. W., et al., Can. J. Microbiol., 39:70–80 (1993), the disclosures of which are incorporated herein by reference.

After transformation into E. coli ER1992, the cells are plated on indicator plates containing X-gal and appropriate antibiotics and incubated overnight at about 30° C. to 42° C. Sometimes none of or not all of the methylation-dependent restriction systems of the host have to be inactivated depending on the particular restriction endonuclease gene or nuclease genes to be cloned. While total deficiency in these systems is not required, it is preferable to use the dinD::lacZ strains deficient in all the methylation-dependent systems to clone a restriction-modification system if one does not know the modified bases (unusually $C^5$ cytosine, $N^4$ cytosine, or $N^6$ adenine).

3) Individual medium/dark blue colonies are picked and inoculated into LB media plus the appropriate antibiotics (10 ml to 1000 ml) and shaken overnight at about 30° C. to 42° C.

4) Cells are harvested by centrifugation, resuspended in sonication buffer plus lysozyme and cell lysis is completed by sonication. Cell debris and insoluble components are removed by centrifugation.

5) If the nuclease gene to be cloned is from a thermostable bacterium, the lysate is heated at about 65° C. for a period of time (for example 30 min) sufficient to denature *E. coli* native proteins. This step efficiently inactivates native *E. coli* nucleases.

6) The supernatant (cell extract) is assayed for nuclease activity on appropriate DNA substrates such as pUC19, pBR322, M13mp18/19 replicative form or single-stranded DNA or λ DNA at 37° C. to 68° C. in an appropriate buffer.

7) DNA digestion patterns or fragments are resolved by agarose gel electrophoresis or PAGE and detected by ethidium bromide staining.

The above-described method has been successfully used to clone a number of nuclease genes including the taqI R gene, the tth111R gene, as well as the gene coding for the DNA nuclease from *Thermus filiformis*. As noted above, this method particularly lends itself to the cloning of other nucleases including thermostable nucleases such as BsoB I from *Bacillus stearothermophilus* (NEB #882). BsoB I is an isoschizomer of Ava I which recognizes CPyCGPuG.

In accordance with another embodiment of the invention, there is provided a novel strain which can be used in the above-described endonuclease indicator method. This strain, *E. coli* ER1992, contains the dinD::lacZ fusion and is deficient in all restriction systems (EcoKR⁻, McrA⁻, McrBC⁻ and Mrr⁻).

*E. coli* ER1992 (F⁻λ⁻Δ(argF-lac)U169 supE44 e14⁻ dinD1::Mu dI1734 (Kanʳ, LacZ⁺) rfbD1? relA1? endA1 spoT1? thi-1 Δ(mcrC-mrr)114::IS10) was constructed in three steps: (i) A Lac⁻ derivative of ER1821 was obtained by transduction with a proC::Tn5 linked to Δ(argF-lac)U169 from NK6993, selecting for Kanʳ and screening for Lac⁻ Pro⁻ to yield ER1984; (ii) this derivative was made Pro⁺ Kanˢ by transduction from ER1578, yielding ER1991; (iii) dinD1::Mu dI1734(Kanʳ, LacZ⁺) was introduced by transduction from JH140, (an *E. coli* strain which is dinD1::Mu dI1734 (Kanʳ, LacZ⁺) (J. Heitman, et al., *Gene* 103:1–9 (1991)) selecting Kanᴿ and screening for nalidixic acid-inducible expression of β-galactosidase mediated by the dinD fusion. This was tested on X-gal plates with a central well containing this DNA-damaging agent. Purified transductants were streaked radially from the well. One that yielded a gradient of dark blue color was designated *E. coli* ER1992. This strain showed light blue color on X-gal in the absence of any DNA damage.

The following examples are given to illustrate embodiments of the present invention as it is presently preferred to practice. It will be understood that these examples are illustrative, and that the invention is not to be considered as restricted thereto except as indicated in the appended claims.

EXAMPLE 1

Cloning of TaqI R Gene in *E. Coli*

Bacterial DNA purification was done as follows: Five grams of *Thermus aquaticus* YT-1 (ATCC 25104) cells were resuspended in 25 ml of buffer containing 25% sucrose, 50 mM Tris-HCl, pH 8.0. Five ml of 0.5M EDTA, pH 8.0, and 6 ml of lysozyme (10 mg/ml) were added to the cell suspension. After 10 min incubation at room temperature, 36 ml of lysis buffer (1% Triton X-100, 50 mM Tris-HCl, pH 8.0, 62 mM EDTA) and 5 ml of 10% SDS were added to completely lyse the cells. Proteins were removed by phenol-CHCl₃ extraction twice and CHCl₃ extraction twice and genomic DNA was precipitated by addition of ¹⁄₁₀ volume of 3.5M sodium acetate and equal volume of isopropanol and centrifugation at 15,000 g. The DNA pellet was washed with 50 ml of 70% ethanol and dried under vacuum. The DNA was resuspended in 10 ml of TE buffer and dialysed in 2 liters of TE buffer overnight at 4° C. Fifty μg of genomic DNA was digested with 1 unit, 0.5 unit, 0.25 unit, 0.125 unit of Sau3AI at 37° C. for 30 min. The digested DNA was purified by phenol-CHCl₃ extraction twice and CHCl₃ extraction twice and ethanol precipitation. Vector pBR322 DNA was linearized by Bam HI restriction enzyme and dephosphorylated by calf intestinal alkaline phosphatase (CIP). The vector DNA was purified again by phenol-CHCl₃ extraction twice and CHCl₃ extraction twice and ethanol precipitation.

Figure 2:
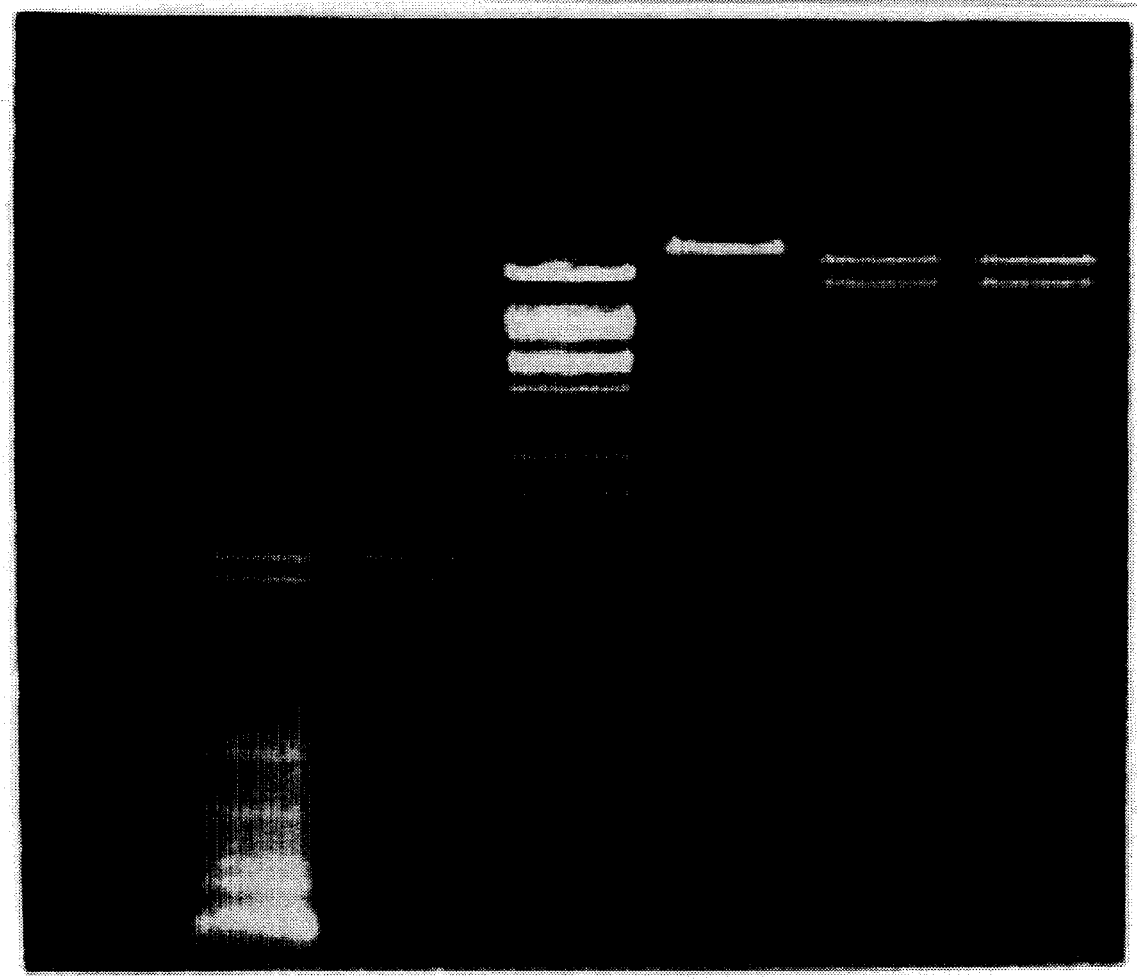
FIG. 2 shows the DNA cleavage pattern produced by cloned Taq I and Tth 111I restriction enzymes produced in E. coli.

The Sau 3AI partially digested genomic DNA was ligated with Bam HI-cleaved and CIP-treated pBR322 DNA. A total of 4,000 colonies were obtained from one transformation experiment by mixing *E. coli* ER1992 (dinD1::lacZ, hsdR, mcrA, mcrBC, mrr) competent cells and the ligated DNA and transformants are plated on Ap plus X-gal plates (5-bromo-4-chloro-3-indolyl-D-galactopyranoside, X-gal, 0.16 mg/ml). Ten blue colonies were found and each inoculated into 10 ml LB plus Ap and incubated overnight at 37° C. in a shaker. Cells were harvested by centrifugation and resuspended in 1 ml of sonication buffer (10 mM Tris-HCl, pH 7.8, 10 mM β-mercaptoethanol) plus lysozyme (10 mg/ml). Cell lysis was completed by sonication. *E. coli* proteins were heat-denatured by incubation of lysate at 65° C. for 30 min. Insoluble components were removed by centrifugation and the supernatant was used for endonuclease activity assay. λ or pBR322 DNA substrates were incubated with 5 μl of cell extract at 65° C. for one hour. DNA fragments were resolved in 0.8% agarose gels and detected by ethidium bromide staining. When cell extracts were examined for endonuclease activity on pBR322 substrate, two strains were found to make Taq I endonuclease (FIG. 2). Plasmid DNA was extracted from these two strains and subjected to Taq I endonuclease digestion. One plasmid was partially resistant to Taq I digestion and the other was completely digested. It was inferred from the above result that one clone contains Taq I methylase gene and the second clone may not.

Plasmid mini-preparation procedure: 1.5 ml overnight culture was pelleted for 3 minutes. The supernatant was poured off and the cell pellet was resuspended in 200 μl STET buffer (50 mM Tris-HCl, pH 7.8, 50 mM EDTA, 0.5% Triton-X100, 8% sucrose). 50 μl of lysozyme (10 mg/ml) was added to the cell suspension. The lysed cells were boiled for 1 min in boiling water and the precipitate was spun down at 14,000 xg, for 10 minutes. The supernatant was removed and extracted with an equal volume of phenol/chloroform (1:1). The layers were separated by centrifugation at 14,000 xg for five minutes. The upper phase was taken into a new centrifuge tube and extracted with equal volume of chloroform. The DNA was mixed with ¹⁄₁₀ volume of sodium acetate and equal volume of isopropanol. The tube was spun at 14,000 xg for 10 minutes to pellet the precipitated nucleic acids. The supernatant was discarded and the pellet was washed with 1 ml of 70% ethanol, repelleted and dried for 15 minutes under vacuum. Once dry, the pellet was resuspended in 100 μl of TE buffer (10 mM Tris-HCl, 1 mM EDTA, pH 8.0).

To estimate Taq I endonuclease yield one liter cell culture was made at 37° C. and cell extract assayed for activity. Both strains make about 5×10⁴ units of Taq I per gram of wet cells. Cell extract was prepared as follows: 1 liter of LB plus Ap was inoculated with 5 ml of overnight cells and shaken at 37° C. overnight. The cells were centrifuged and cell pellet resuspended in 20 ml sonication buffer (10 mM Tris-HCl, 10 mM β-mercaptoethanol), sonicated for ten times at 30 seconds burst, centrifuged at 15000 xg for 30 minutes to remove cell debris. The supernatant was assayed for endonuclease activity.

EXAMPLE 2

Cloning of TTH111IR Gene

Genomic DNA was prepared from *Thermus thermophilus* 111 strain which produces Tth 111I restriction enzyme. Five grams of cells were resuspended in 25 ml of buffer containing 25% sucrose, 50 mM Tris-HCl, pH 8.0. Five ml of 0.5M EDTA, pH 8.0, and 6 ml of lysozyme (10 mg/ml) were added to the cell suspension. After 10 min incubation at room temperature, 36 ml of lysis buffer (1% Triton X-100, 50 mM Tris-HCl, pH 8.0, 62 mM EDTA) and 5 ml of 10% SDS were added to completely lyse the cells. Proteins were removed by phenol-CHCl$_3$ extraction twice and CHCl$_3$ extraction twice and genomic DNA was precipitated by addition of 1/10 volume of 3.5M sodium acetate and equal volume of isopropanol and centrifugation at 15,000 g. The DNA pellet was washed with 50 ml of 70% ethanol and dried under vacuum. The DNA was resuspended in 10 ml of TE buffer and dialysed in 2 liters of TE buffer overnight at 4° C. Fifty μg of genomic DNA was digested with 1 unit, 0.5 unit, 0.25 unit, 0.125 unit of Sau 3AI at 37° C. for 30 min. The digested DNA was purified by phenol-CHCl$_3$ extraction twice and CHCl$_3$ extraction twice and ethanol precipitation. Vector pBR322 DNA was linearized by BamHI restriction enzyme and dephosphorylated by calf intestinal alkaline phosphatase (CIP). The vector DNA was purified by phenol-CHCl$_3$ extraction twice and CHCl$_3$ extraction twice and ethanol precipitation. The Sau 3AI partially digested genomic DNA was ligated with Bam HI-cleaved and CIP-treated pBR322 DNA. The DNA ligation mixture was transformed into *E. coli* ER1992 (dinD1::lacZ, hsdR, mcrA, mcrBC, mrr) competent cells. Forty blue colonies were found among 8,000 transformants. These forty strains were checked for endonuclease activity. Fourteen strains make Tth 111I endonuclease (FIG. 2). Plasmid DNA from Tth 111I-producing strains were prepared and subjected to Tth 111I restriction digestion. Twelve plasmids were linearized by Tth 111I endonuclease, suggesting either methylase gene is not contained in the same fragment or it is not expressed 37° C. Three plasmids were partially resistant to Tth 111I, indicating the presence of the cognate methylase gene on the cloned fragment.

EXAMPLE 3

Cloning of EcoO109IR Gene by Combination of Methylase Selection Method and Blue Colony Screening Method In this Example, the possibility of combining the methylase selection method and the endonuclease indicator method for cloning of restriction endonuclease gene was tested. Genomic DNA of *E. coli* H709c was prepared as described in Example 1. The DNA was cleaved partially with Sau 3AI as described in Example 1 and ligated to pBR322 (Bam HI linearized and CIP treated) at 16° C. overnight. The ligation mixture was used to transform *E. coli* RR1 competent cells. A total of 10$^5$ transformants were pooled and inoculated into 500 ml LB medium. The cell culture was shaken overnight at 37° C. Bacterial cells were harvested by centrifugation and resuspended in 20 ml of buffer P1 (100 μg/ml RNAseA, 50 mM Tris-HCl, 10 mM EDTA, pH 8.0). Following addition of 20 ml buffer P2 (200 mM NaOH, 1% SDS) and incubation at room temperature for five min, 20 ml of buffer P3 was added (2.55M KAc, pH 4.8). The precipitates were removed by centrifugation at 4° C. for 30 min (20,000 xg). The supernatant was loaded into two Qiagen midi-columns preequilibrated with buffer QBT (750 mM NaCl, 50 mM MOPS, 15% ethanol, pH 7.0, 0.15% Triton X-100). The plasmid DNA was washed with 20 ml of buffer QC (1M NaCl, 50 mM MOPS, 15% ethanol, pH 7.0) and eluted with 5 ml of buffer QF (1.25 mM NaCl, 50 mM MOPS, 15% ethanol, pH 8.2). The plasmid DNA was precipitated with equal volume of isopropanol and centrifugation at 4° C. for 30 min. The DNA pellet was washed with 70% ethanol, dried under vacuum, and dissolved in 1 ml of TE buffer. Ten μg of plasmid DNA from the plasmid library was digested with 100 units of Eco O109I restriction enzyme at 37° C. for three hours. The digested plasmid DNA was used to transform *E. coli* ER1992 (dinD1::lacZ, hsdR, mcrA, mcrBC, mrr) and cells are plated on X-gal plus Ap plates. Fourteen blue colonies were found among 120 transformants. Ten ml of cell culture was made from each of 14 strains and cell extracts prepared (as described in Example 1) to assay for Eco O109I endonuclease activity on λ DNA substrate. Eight strains were found to make Eco O109I restriction endonuclease. By combining the methylase selection method and the endonuclease indicator method one could eliminate those clones that only carry methylase gene or lost cleavage sites after challenge but identify those clones that carry endonuclease gene alone or together with the methylase gene.

EXAMPLE 4

Cloning of a Gene Coding For a Thermostable DNA Nuclease

Genomic DNA from strain *Thermus filiformis* was prepared as described in Example 1. The DNA was cleaved partially with Sau 3AI as described in Example 1 and ligated to pBR322 (Bam HI linearized and CIP treated) at 16° C. overnight. The ligation mixture was used to transform *E. coli* ER1992 competent cells and plated on X-gal, Amp plates. A total of 8,000 transformants were obtained from one transformation experiment. Among these transformants, twenty-three blue colonies were found. Ten ml of cell culture were made from each of the 23 blue isolates and cell extracts prepared (as described in Example 1) to assay for DNA nuclease activity on pBR322 DNA substrate. The cell extract from one isolate named Tfi#17 displayed DNA nicking activity on pBR322 double-stranded DNA at 68° C. incubation temperature. To further test the nuclease activity, M13mp18 RF form (double-stranded DNA) and single-stranded form were used as the substrates. Again, the nuclease shows DNA nicking activity on the double-stranded substrate. The single-stranded DNA were degraded with the addition of the nuclease. When double-stranded DNA (lambda DNA or M13 RF form) were incubated with the nuclease for a long period of time (12 hours), the DNA was also degraded. Therefore, we concluded the preferred substrate for Tfi#17 nuclease is single-strand DNA. We also tested that the nuclease can be used for unidirectional deletion application such as after exonuclease III digestion of double-stranded DNA, the remaining single-stranded DNA can be removed by the Tfi#17 nuclease.

What is claimed is:

1. A method for isolating DNA coding for a nuclease comprising the steps of:
   (a) forming a DNA library from a source coding for the nuclease;
   (b) ligating the DNA of step (a) into an appropriate cloning vector;
   (c) transforming the host cell which (i) contains a DNA damage-inducing promoter fused to an indicator/reporter gene, and (ii) is deficient in one or more methylation-dependent restriction systems with the cloning vector of step (b);
   (d) plating and incubating the transformed host cells of step (c) on indicator plates containing a substrate which reacts with the expression product of the indicator/reporter gene and appropriate antibiotics;
   (e) selecting appropriate colonies from the plated transformed host cells of step (d) and growing said cells in an appropriate medium;
   (f) harvesting and breaking open the cells of step (e) followed by removal of all debris and other insoluble components to produce a supernatant; and
   (g) assaying the supernatant of step (f) for nuclease activity on appropriate DNA substrates in an appropriate buffer.

2. The method of claim 1, wherein the DNA damage-inducing promoter fused to the indicator/reporter gene is dinD1::lacZ.

3. The method of claim 2, wherein the substrate which reacts with the expression product of the indicator/reporter gene is X-gal.

4. The method of claim 2, wherein the selection of step (c) is effected by choosing medium to dark blue colonies.

5. The method of claim 1, wherein the nuclease is a restriction endonuclease.

6. The method of claim 1, wherein the host cell is deficient in all methylation-dependent restriction systems.

7. The method of claim 1, wherein the host cell of step (c) is a strain of *E. coli*.

8. The method of claim 6, wherein the host cell is *E. coli* ER1992.

9. A host cell for cloning a nuclease, wherein the host cell contains a DNA damage-inducing promoter fused to an indicator/reporter gene and which is deficient in all methylation-dependent restriction systems.

10. The host cell of claim 9, wherein the host cell is a strain of *E. coli*.

11. The host cell of claim 10, wherein the host cell is *E. coli* ER1992.

12. The method of claim 1, wherein the nuclease is thermostable nuclease and wherein the transformation of step (c) is conducted at a temperature of between about 30° to 42° C.

* * * * *

UNITED STATES PATENT AND TRADEMARK OFFICE
CERTIFICATE OF CORRECTION

PATENT NO. : 5,498,535
DATED : March 12, 1996
INVENTOR(S) : Fomenkov, et al

It is certified that error appears in the above-indentified patent and that said Letters Patent is hereby corrected as shown below:

Column 1, line 56, replace "Eco RII" with --*Eco*RII--

Column 1, line 57, replace "Hha II" with --*Hha*II--

Column 1, line 58, replace "Pst I" with --*Pst*I--

Column 2, line 3, replace "Eco RV" with --*Eco*RV--

Column 2, line 5, replace "Pae R7" with --*Pae*R7--

Column 2, line 6, replace "Pvu II" with --*Pvu*II--

Column 2, line 11, replace "Bsu RI" with --*Bsu*RI--

Column 2, line 16, replace "Bsp RI" with --*Bsp*RI--

Column 2, line 17, replace "Bcn I" with --*Bcn*I--

Column 2, line 18, replace "Bsu RI" with --*Bsu*RI--

Column 2, line 19, replace "Msp I" with --*Msp*I--

Column 2, line 25, replace "9; Kelleher" with --9 (1991); Kelleher--

Column 3, line 11, replace "Eco RI, or Bam HI" with --*Eco*RI, or *Bam*HI--

UNITED STATES PATENT AND TRADEMARK OFFICE
CERTIFICATE OF CORRECTION

PATENT NO. : 5,498,535            Page 2 of 8
DATED : March 12, 1996
INVENTOR(S) : Fomenkov, et al It is certified that error appears in the above-indentified patent and that said Letters Patent is hereby corrected as shown below:

Column 3, line 55, replace "Taq I" with --*TaqI*--

Column 3, line 55, replace "Tth 111I" with --*Tth*111I--

Column 4, line 2, replace "Taq I and Tth 111I" with --*TaqI* and *Tth*111I--

Column 4, line 34, replace "dinA" with --*dinA*--

Column 2, line 26, replace "dinD1::lacZ" with --*dinD1::lacZ*--

Column 2, line 27, replace "dinD1" with --*dinD1*--

Column 2, line 38, replace "mcrA, mcrBC mrr and carrying the dinD1::lacZ" with --*mcrA, mcrBC, mrr* and carrying the *dinD1::lacZ*--.

Column 3, line 3, replace "dinD1::lacZ" with --*dinD1::lacZ*--

Column 3, line 8, replace "dinD1::lacZ" with --*dinD1::lacZ*--

Column 3, line 18, replace "dinD1::lacZ" with --*dinD1::lacZ*--

Column 3, line 34, replace "dinD1::lacZ" with --*dinD1::lacZ*--

UNITED STATES PATENT AND TRADEMARK OFFICE
CERTIFICATE OF CORRECTION

PATENT NO. : 5,498,535
DATED : March 12, 1996
INVENTOR(S) : Fomenkov, et al

It is certified that error appears in the above-indentified patent and that said Letters Patent is hereby corrected as shown below:

Column 3, last line, replace "Tth111I" with --*Tth*111I--

Column 3, line 38, replace "in vivo" with --*in vivo*--

Column 3, line 61, replace "ecoO109IR" with --*eco*O109IR--

Column 3, line 66, replace "tth111IR" with -- *tth*111IR--

Column 4, line 1-3, replace "FIG. 2 shows the DNA cleavage pattern produced by cloned Taq I and Tth 111I restriction enzymes produced in *E. coli*" with
--Figure 2 shows the DNA cleavage pattern produced by cloned *Taq*I and *Tth*111I restriction enzymes produced in *E. coli*. This Figure shows the assay of *Taq*I and *Tth*111I endonuclease activity in cell extracts. Lane 1, uncut pBR322 DNA; lane 2, pBR322 cleaved with cell extract containing *Taq*I endonuclease; lane 3, pBR322 cleaved with purified *Taq*I; lane 4, *Bst*EII cleaved λ DNA size standard; lane 5, uncut λ DNA; lane 6 λ DNA cleaved with cell extract containing *Tth*111I endonuclease; lane 7, λ DNA cleaved with purified *Tth*111I endonuclease. *Taq*I and *Tth*111I restriction digestions were performed at 65°C for one hour.--

UNITED STATES PATENT AND TRADEMARK OFFICE
CERTIFICATE OF CORRECTION

PATENT NO. : 5,498,535
DATED : March 12, 1996
INVENTOR(S) : Fomenkov, et al

It is certified that error appears in the above-indentified patent and that said Letters Patent is hereby corrected as shown below:

Column 4, line 25, replace "dinD1::lacZ" with
--*dinD1::lacZ*--

Column 4, line 26-27, replace "dinD1::lacZ, hsdR, mcrA, mcrBC, mrr" with --*dinD1::lacZ, hsdR, mcrA, mcrBC, mrr*--

Column 4, line 55, replace "dinD1::lacZ" with
--*dinD1::lacZ*--

Column 5, line 16, replace "tth111R" with --*tth111R*--

Column 5, line 25, replace "dinD1::lacZ" with
--*dinD1::lacZ*--

Column 5, line 28, replace (argF-lac)U169 supE44" with
--*(argF-lac)U169 supE44*--

Column 4, line 35, replace "dinG" with --*dinG*--

Column 4, line 39, replace "phoA" with --*phoA*--

Column 4, line 40, replace "lux" with --*lux*--

Column 5, line 15, replace "taqI R" with --*taqIR*--

UNITED STATES PATENT AND TRADEMARK OFFICE
CERTIFICATE OF CORRECTION

PATENT NO. : 5,498,535            Page 5 of 8
DATED : March 12, 1996
INVENTOR(S) : Fomenkov, et al It is certified that error appears in the above-indentified patent and that said Letters Patent is hereby corrected as shown below:

Column 5, line 17, replace "*filiformus*" with --*filiformis*--

Column 5, line 19, replace "BsoB I" with --*BsoBI*--

Column 5, line 20, replace "BsoB I" with --*BsoBI*--

Column 5, line 21, replace "Ava I" with --*AvaI*--

Column 5, line 55, replace "TaqI R" with --*taqIR*--

Column 6, line 9, replace "Bam HI" with --*BamHI*--

Column 6, line 14, replace "Sau 3AI" with --*Sau3AI*--

Column 6, line 16, replace "Bam HI" with --*BamHI*--

Column 6, line 35, replace "Taq I" with --*TaqI*--

Column 6, line 37, replace "Taq I" with --*TaqI*--

Column 6, line 38, replace "Taq I" with --*TaqI*--

Column 6, line 40, replace "Taq I" with --*TaqI*--

Column 6, lne 63, replace "Taq I" with --*TaqI*--

UNITED STATES PATENT AND TRADEMARK OFFICE
CERTIFICATE OF CORRECTION

PATENT NO. : 5,498,535  
DATED : March 12, 1996  
INVENTOR(S) : Fomenkov, et al

Page 6 of 8

It is certified that error appears in the above-indentified patent and that said Letters Patent is hereby corrected as shown below:

```
Column 5, line 29, replace "dinD1" with --dinD1--

Column 5, lines 29-30, replace "rfbD1? relA1? endA1 spoT1?
        thi-1" with --rfbD1? relA1? endA1 spoT1? thi-1--

Column 5, line 30, replace "mcrC-mrr" with --mcrC-mrr--

Column 5, line 32, replace "proC" with --proC--

Column 5, line 32, replace "argF-lac)U169" with
        --argF-lac)U169--

Column 5, line 36, replace "dinD1" with --dinD1--

Column 5, line 37, replace "dinD1" with --dinD1--

Column 5, line 41, replace "dinD" with --dinD--

Column 6, line 7, replace "Sau3AI" with --Sau3AI--

Column 6, lines 18-19, replace "dinD1::lacZ, hsdR, mcrA,
        mcrBC, mrr" with --dinD1::lacZ, hsdR, mcrA,
        mcrBC, mrr--

Column 7, line 19, replace "lyse" with --lysed--

Column 7, line 31, replace "BamHI" with --BamHI--

Column 7, lines 38-39, replace "dinD1::lacZ, hsdR,
        mcrA, mcrBC, mrr" with --dinD1::lacZ, hsdR,
        mcrA, mcrBC, mrr--

Column 7, line 60, after "H709c" insert --(EcoO109I)--
```

UNITED STATES PATENT AND TRADEMARK OFFICE
CERTIFICATE OF CORRECTION

PATENT NO.  : 5,498,535
DATED       : March 12, 1996
INVENTOR(S) : Fomenkov, et al It is certified that error appears in the above-indentified patent and that said Letters Patent is hereby corrected as shown below:

Column 6, line 65, replace "Taq I" with --*Taq*I--

Column 7, line 10, replace "TTH111IR" with --*tth111IR*--

Column 7, line 12, replace "Tth 111I" with --*Tth*111I--

Column 7, line 28, replace "Sau 3AI" with --*Sau*3AI--

Column 7, line 35, replace "Sau 3AI" with --*Sau*3AI--

Column 7, line 42, replace "Tth 111I" with --*Tth*111I--

Column 7, line 42-43, replace "Tth 111I" with --*Tth*111I--

Column 7, line 43-44, replace "Tth 111I" with --*Tth*111I--

Column 7, line 45, replace "Tth 111I" with --*Tth*111I--

Column 7, line 47, replace "Tth 111I" with --*Tth*111I--

Column 7, line 53, replace "Eco0109IR" with --*eco0109IR*--

Column 7, line 62, replace "Sau 3AI" with --*Sau*3AI--

Column 7, line 63, replace "Bam HI" with --*Bam*HI--

UNITED STATES PATENT AND TRADEMARK OFFICE
CERTIFICATE OF CORRECTION

PATENT NO. : 5,498,535
DATED : March 12, 1996
INVENTOR(S) : Fomenkov, et al

It is certified that error appears in the above-indentified patent and that said Letters Patent is hereby corrected as shown below:

Column 8, line 18, replace "Eco 0109I" with --*Eco*0109I--

Column 8, line 25, replace "Eco 0109I" with --*Eco*0109I--

Column 8, line 26, replace "Eco 0109I" with --*Eco*0109I--

Column 8, line 41, replace "Sau 3AI" with --*Sau*3AI--

Column 8, line 42, replace "Bam HI" with --*Bam*HI--

Column 8, lines 20-21, replace "dinD1::lacZ, hsdR, mcrA, mcrBC, mrr" with --*dinD1::lacZ, hsdR, mcrA, mcrBC, mrr*--

Column 9, last line, replace "dinD1::lacZ" with --*dinD1::lacZ*--

Signed and Sealed this

Fifteenth Day of October, 1996

BRUCE LEHMAN

*Attest:*

*Attesting Officer*   Commissioner of Patents and Trademarks